US010806846B2

(12) United States Patent
Turner

(10) Patent No.: US 10,806,846 B2
(45) Date of Patent: Oct. 20, 2020

(54) CONTROL SYSTEM

(71) Applicant: Spectrum Medical Ltd., Gloucester (GB)

(72) Inventor: Stephen Turner, Gloucester (GB)

(73) Assignee: Spectrum Medical Ltd., Gloucester (GB)

( * ) Notice: Subject to any disclaimer, the term of this patent is extended or adjusted under 35 U.S.C. 154(b) by 314 days.

(21) Appl. No.: 15/763,660

(22) PCT Filed: Sep. 8, 2016

(86) PCT No.: PCT/GB2016/052777
§ 371 (c)(1),
(2) Date: Mar. 27, 2018

(87) PCT Pub. No.: WO2017/055796
PCT Pub. Date: Apr. 6, 2017

(65) Prior Publication Data
US 2018/0264187 A1 Sep. 20, 2018

(30) Foreign Application Priority Data
Sep. 29, 2015 (GB) .................................. 1517201.8

(51) Int. Cl.
*A61M 1/36* (2006.01)

(52) U.S. Cl.
CPC ........ *A61M 1/3639* (2013.01); *A61M 1/3621* (2013.01); *A61M 1/3666* (2013.01);
(Continued)

(58) Field of Classification Search
CPC .............. A61M 1/3621; A61M 1/3639; A61M 1/3664; A61M 1/3666; A61M 2205/3331; A61M 2205/3341; A61M 2205/3365
See application file for complete search history.

(56) References Cited

U.S. PATENT DOCUMENTS 5,385,540 A 1/1995 Abbott et al.
5,645,531 A 7/1997 Thompson et al.
(Continued)

FOREIGN PATENT DOCUMENTS

RU 2 570 391 12/2015
WO WO2017/046567 A2 3/2017

OTHER PUBLICATIONS

United Kingdom Intellectual Property Office, Search Report under Section 17(5)—Application No. GB1517201.8, 1 page (dated Mar. 2, 2016).
(Continued)

*Primary Examiner* — Leslie R Deak
(74) *Attorney, Agent, or Firm* — Sunstein LLP

(57) ABSTRACT

A control system controlling the line pressure in a blood supply system (1) in which a pump (14) pumps blood from a reservoir (10) via a primary passage (18) toward a plurality of outlets (16, 26, 26a), wherein one or more outlets are openable to permit flow and closable to block flow, said control system comprises a monitoring arrangement to determine a line pressure in the primary passage, and a controller responsive to the monitoring arrangement and controlling the pump (14) to maintain the line pressure in the primary passage (18) above a pre-set level. The control system practically eliminates the risk of a momentary reduction in blood supply line pressure when an outlet is opened.

22 Claims, 2 Drawing Sheets

(52) U.S. Cl.
CPC ... *A61M 1/3664* (2013.01); *A61M 2205/3331* (2013.01); *A61M 2205/3341* (2013.01); *A61M 2205/3365* (2013.01)

(56) References Cited

U.S. PATENT DOCUMENTS

| | | |
|---|---|---|
| 5,957,137 A | 9/1999 | Dalke et al. |
| 2005/0084416 A1 | 4/2005 | Thomas |
| 2014/0099235 A1 | 4/2014 | Ellingboe et al. |
| 2014/0271356 A1 | 9/2014 | Samolyk |

OTHER PUBLICATIONS

European Patent Office, International Search Report—Application No. PCT/GB2016/052777, 12 pages (dated Dec. 9, 2016), together with the Written Opinion of the International Searching Authority.

CONTROL SYSTEM

FIELD OF THE INVENTION

The present invention relates to a blood supply control system. More specifically, the present invention relates to a control system for controlling the line pressure in a blood supply system with a main supply channel and one or more secondary supply channels.

BACKGROUND

External blood circulation systems are used during surgery or external ventilation. A typical blood circulation system comprises a venous blood line that collects blood from a patient into a reservoir. From the reservoir, blood is pumped via a main blood line through various components, such as an oxygenator, to condition (e.g., oxygenate, set pressure and/or temperature) the blood for supply to a patient, and supplied to a patient in the conditioned form.

Blood from the main blood line, whether or not conditioned, may also be used for other applications, e.g., as a carrier fluid for cardioplegia, or for perfusion of specific organs (e.g., cerebral perfusion). Blood in the main line is typically pumped at a flow rate in the region of 5 litres per minute (l/min) and at a driving pressure above atmospheric pressure. The logistics of supplying the correct amounts of blood at the desired flow rate and pressure, within narrow safety margins, are challenging.

The present invention seeks to improve the management of line pressures in a blood supply system.

SUMMARY OF THE INVENTION

In accordance with a first aspect of the present invention, there is provided a control system controlling the line pressure in a blood supply system as defined in claim 1.

In the blood supply system, a first pump is provided to pump blood from a reservoir via a primary passage at a flow rate and at a driving pressure toward a plurality of outlets, wherein one or more of the outlets are openable to permit flow through the outlet and closable to block flow through the outlet.

The control system comprises a monitoring arrangement to determine a pressure value representative of a line pressure in the primary passage, and a controller responsive to the monitoring arrangement. The controller is configured to control the first pump to maintain the line pressure in the primary passage above a pre-set level.

The blood supply system may be part of a perfusion system of the type used during open heart surgery. The primary passage may be constituted by the arterial line, or "main" line, i.e. the line downstream of a blood reservoir from where blood is conditioned for supply to a patient.

The reservoir holds blood in an unpressurised condition (i.e., at ambient/atmospheric pressure, typically in a flexible pouch or hard shell). The first pump is located in the main line and withdraws blood from the reservoir and brings the blood from the reservoir to the required flow rate and driving pressure. The blood is pumped at the flow rate and pressure through components of the perfusion system, such as an oxygenator, and conditioned for subsequent delivery to a patient, and driven towards the outlets of the system.

The first pump may be understood as any arrangement that is configured to generate flow towards the outlets and that may be controlled to modulate the flow rate. This may be a positive displacement pump, such as a peristaltic pump (roller pump). This may be a non-occlusive pump such as a centrifugal pump.

An outlet may be understood as a point at which the blood is in a condition for subsequent administration to a patient. E.g., the blood may be oxygenated, and have a pre-determined pressure, temperature, and/or flow rate.

The main line constitutes a primary passage for supply of conditioned blood to a patient. One or more outlets from the main line may constitute diversions, or offtakes, from the primary passage into secondary passages, e.g. a cardioplegia line (a line for delivering heart-suppressing agent) or a cerebral perfusion line (line for supplying blood directly to the brain). This affects the flow rate and/or the driving pressure in the main line downstream of the diversion. The pressure in the main line may increase, for instance, if additional lines are clamped. The pressure in the main line may decrease if more diversions are opened. The effect of a diversion on the driving pressure in the main line is more pronounced at low flow rates.

To illustrate the magnitudes involved with examples, the pressure in a main line of a perfusion system may routinely be in a range of 200 to 300 mmHg (26.7 to 40.0 kPa), as opposed to the mean coronary pressures in the region of 20 to 120 mmHg (2.67 to 16.0 kPa). In the field, pressures are conventionally provided in mmHg relative to atmospheric pressure (1 atm corresponds to 101.325 kPa, or 760 mmHg). A blood pressure of 100 mmHg (above atmospheric pressure) would correspond to a total pressure of 860 mmHg. If the line pressure in a main line is above atmospheric pressure, e.g. at 20 mmHg, it can be deducted that the first pump is running.

The driving pressure, i.e., the pressure required to deliver a fluid towards a patient, may depend on various factors, including the posture of a patient and the body location at which the cardioplegic solution is to be administered. The minimum driving pressure may be as low as about 20 mmHg but will typically be higher and depend on pressure levels inside the patient. Arterial blood leaving the oxygenator at a pressure of about 200 to 300 mmHg can be assumed to have sufficient driving pressure in order to achieve the desired blood flow rates towards (and into) a patient.

The pre-set level may be set at an appropriate level above atmospheric pressure. For instance, the pre-set level may be at least 20, 30, 40, 50, 60, 70, 80, 90, or 100 mmHg above atmospheric pressure.

Blood needs to be administered to a patient at an appropriate flow rate and at an appropriate driving pressure, each within narrow margins. Over-pressurising increases the strain on the components of the delivery system. Over-pressurising may also be hazardous to a patient, for instance, by causing damage to tissues. Under-pressurising is a problem because this may result in back flow.

The flow rate of blood to a patient during perfusion may be in the region of o 5 litres per minute (l/m), and at a driving pressure sufficient to ensure blood flow into the patient.

The flow rate may have to be adjusted for specific organs. E.g., a cerebral perfusion line may be operated at about 0.5 l/m, i.e., a magnitude lower than total body perfusion.

Several components may be supplied from the main line. During open heart surgery, heart beat is suppressed by cardioplegic agent, which is typically administered via a cardioplegia line often using blood as a carrier fluid. The blood is typically diverted from the main blood line as and when cardioplegic agent needs to be administered. A typical flow rate in a cardioplegia line is in the region of 0.2 to 0.3 l/m. If the cardioplegia carrier fluid is blood diverted from the main arterial line, this may affect the pressure and flow rate of the blood supplied to other organs. For instance, during cerebral perfusion at 0.5 l/m, a diversion of 0.2 to 0.3 l/m amounts to a significant offtake.

The activation of a diversion risks a momentary reduction in line pressure which can have adverse consequences on the pressure gradient in the main line. This may result in insufficient driving pressure and/or a negative pressure gradient across the oxygenator. This can have serious, even fatal effects. For instance, without sufficient line pressure, the air pressure gradient across the oxygenator may favour air bubbles becoming entrained in the blood, which may cause air embolism (blocking of blood vessels by an air bubble). Air bubbles in the blood may, thus, pose a hazard to a patient if the blood is subsequently administered to the patient. Air bubbles in blood, if subsequently administered to a patient, may prolong patient post-operation recovery times, may be responsible for causing embolic ischemic events such as stroke, and even cause death. Also, air bubbles may interfere with blood measurements.

There are different strategies to ensure blood supply to vital organs while the heart is bypassed. This may be achieved, e.g., by stopping (clamping) the main arterial line (that would normally supply blood to the heart) and opening, upstream of the clamp, a diversion from the main arterial line. Another option is to repurpose the main arterial line and connect it directly to a line supplying the brain.

An arrangement that allows the pressure in the primary passage to be maintained above a pre-set pressure reduces, and for practical purposes eliminates, the risk of a negative pressure gradient. This can be achieved regardless of the strategy selected to supply blood to a patient.

A mechanism to maintain the pressure at a pre-determined level may be regarded as a closed loop control. The closed loop control provides a more responsive mechanism to prevent an unsafe pressure situation, or an unsafe pressure gradient. This increases the safety of the perfusion system.

The closed loop control provides a responsive mechanism to maintain a pre-set pressure level regardless of the number diversions being opened or closed. This allows more diversions to be considered. This increases the versatility of the perfusion system.

The line pressure may be high enough to safely initiate a diversion into a secondary passage if the first pump is not active. For instance, in clinical practice it may happen that all lines are clamped before the first pump is stopped, and until the firsts pump stops, the pressure level in the main line may increase. The monitoring arrangement will be able to determine whether or not the pressure level is above the pre-set level. If the pressure level is above the pre-set level, the control system may determine that it is not necessary to start the first pump when a blood diversion is activated, as long as the pre-set pressure level is maintained. If the pressure level is not above the pre-set level, the control system provides that the first pump is operated to maintain the pressure level above the pre-set level. This allows blood diversions to be initiated even though the first pump may not yet be running.

The monitoring arrangement may continuously measure line pressure. This improves the response time of the closed loop control.

In some embodiments, the controller is configured to control the first pump to maintain the line pressure in the primary passage above a minimum driving pressure, below a maximum driving pressure, and/or at a driving pressure.

The expressions "back flow" and "retrograde flow" may be used interchangeably in day-to-day language, and even in the surgical field.

By "back flow", it is meant that a fluid flows in a direction opposite of the intended direction. E.g., in a channel intended for delivery of a fluid from a supply reservoir toward a pump, the fluid would flow toward the supply reservoir in the event of back flow.

By "retrograde" flow, it is meant that a fluid is purposefully channelled to flow in a direction other than a conventional arterial-to-venous direction. Specifically, retrograde flow may be in a venous-to-arterial direction.

Put briefly, back flow is undesired, whereas retrograde flow is purposive. In a retrograde flow channel in which it is intended to deliver a fluid toward a patient (e.g., from a pump), back flow means that the fluid flows from the patient (e.g., toward the pump).

By "minimum driving pressure", it is meant that the pressure is sufficiently high to avoid back flow.

By "maximum driving pressure", it is meant that the pressure is at safe level to avoid tissue damage or pump circuit damage.

The maximum driving pressure may be set relative to the maximum main line pressure. A perfusion system may, for safety reasons, be operated with a maximum main line pressure. The maximum main line pressure may be 300 mmHg. The maximum driving pressure may be set at the same level as the maximum main line pressure. The maximum driving pressure may be set at a level below the maximum main line pressure. The maximum driving pressure may be set at an appropriate level below the maximum main line pressure. For instance, the maximum driving pressure level may be set at least 20, 30, 40, 50, 60, 70, 80, 90, or 100 mmHg below the maximum main line pressure.

The driving pressure range may be defined by the minimum and maximum driving pressure, i.e., a range between the minimum and maximum driving pressure set points.

The minimum and maximum values for the driving pressure may be set according to clinical requirements. This may depend, e.g., on the ambient pressure, blood viscosity, temperature, flow rates, cannula sizes, patient posture, and/or patient position. The minimum driving pressure may not necessarily be set at the minimum level necessary to ensure a positive pressure gradient. The minimum driving pressure may include a margin, e.g. at least 20, 30, 40, 50, 60, 70, 80, 90, or 100 mmHg above such a minimum level, to ensure safe operation of the control system.

In some embodiments, the controller is configured to receive as an input the pressure value and comprises decision logic for determining a difference between the pressure value and the pre-set level, and for issuing a signal to operate the first pump at pump parameters to reduce the difference, to adjust the line pressure in the primary passage to the pre-set level.

Such a mechanism facilitates modulating the first pump to stay above a pre-set level or within pre-set (minimum or maximum) boundaries. This facilitates the integration of the control system with existing pump types.

The decision logic may be configured to determine the difference between the pressure value and the pre-set pressure level if the pressure value is below the minimum. The decision logic may be configured to determine the difference between the pressure value and the maximum driving pressure range if the pressure value is above the maximum.

In some embodiments, the decision logic is configured to reduce the difference by calculating an offset value representing a change of pump parameters effective to adjust the line pressure in the primary passage to the pre-set level, and by generating the signal on the basis of the offset value.

An offset value is a value proportionate to the difference between the (actual) line pressure and the driving pressure. Providing a control signal to the pump to alter pump operation in proportion to the measured difference increases the responsiveness and the accuracy of the control system.

In some embodiments, the system comprises one or more outlet pumps, each outlet pump provided to transport blood through an outlet of the plurality of outlets, wherein the controller is configured to modulate operation of at least one outlet pump if the pressure value is below the pre-set level.

The outlet pumps may be operational to divert blood from the primary passage (e.g., the main arterial line) through outlets. An example is a cardioplegia line pump for flowing cardioplegic agent carrier fluid. Other examples are diversions for purging lines or for a hemoconcentrator.

The controller may modulate the operation of one or more outlet pumps to limit, or mitigate, the effect of any blood diversions on the line pressure in the primary passage.

In certain scenarios it can be assumed that blood supply via blood diversions is less critical than the need to ensure blood supply at appropriate conditions via the primary passage. For instance, it may be acceptable to reduce and/or delay the flow rate of a cardioplegia carrier fluid for a few seconds, to allow time for the first pump to increase line pressure, until it is safe to operate the cardioplegia line at its proper flow rate.

The controller may modulate a plurality of outlet pumps. The controller may ensure that outlet pumps activate subsequently, or staggered, to avoid a contemporaneous diversion of blood from the main line. This is particularly suitable for non-time-critical blood diversion. This allows a large number of non-time-critical diversions to be connected to the primary passage without compromising safe operation.

Furthermore, the provision of a closed loop control allows a margin for the minimum driving pressure to be smaller, because risk of a blood diversion causing a negative line pressure is reduced.

In some embodiments, the controller is configured to modulate operation of at least one outlet pump prior to modulating operation of the first pump.

The line pressure may be maintained by modulating the first pump and/or by modulating any outlet pumps. E.g., to ensure a line pressure above a minimum driving pressure, the first pump speed may be increased, and/or the outlet pumps may be stopped. Modulating the outlet pumps prior to the first pump allows a more steady operation of the first pump. This reduces the likelihood of a pulsating flow due to continual modulation of the first pump.

In some embodiments, the controller is configured to prevent operation of at least one outlet pump if the pressure value is below the pre-set level.

The controller may be configured to prevent opening of one or more specific diversions, or of all diversions, from the primary passage while there is not sufficient line pressure in the primary passage.

In some embodiments, the controller is configured to control the first pump by modulating revolutions per minute of the first pump.

The controller may operate a peristaltic pump (roller pump) to reduce the likelihood of a negative line pressure gradient.

In some embodiments, the monitoring arrangement comprises one or more pressure sensors.

The sensors may be non-contact sensors. Non-contact sensors allow a determination of the quantity of blood to be made without coming into physical contact with the blood. Non-contact sensors facilitate the taking of frequent or continuous measurements. Also, non-contact sensors reduce the risk of contamination.

In some embodiments, the monitoring arrangement is configured to measure the line pressure downstream of the first pump.

In some embodiments, the monitoring arrangement is configured to measure the line pressure upstream of an oxygenator.

This ensures that an appropriate line pressure is maintained upstream of the oxygenator. This may be appropriate for certain oxygenator types.

To provide an illustrative example, a pressure differential across an oxygenator during total body perfusion may be in the region of 50 to 75 mmHg. I.e., the pre-oxygenator line pressure may be in the region of 300 mmHg and the post-oxygenator line pressure may be in the region of 225 mmHg. During low-flow conditions, the pressure differential across the oxygenator may be in the region of 5 to 10 mmHg.

The pre-set level may be set depending on the location at which the monitoring arrangement measures line pressure.

In some embodiments, the monitoring arrangement is configured to measure the line pressure downstream of an oxygenator.

This ensures that an appropriate line pressure is maintained downstream of the oxygenator. This ensures that the line pressure of the blood leaving the oxygenator is appropriate. Diversions downstream of the oxygenator may cause a negative pressure gradient across the oxygenator, more specifically, across the barriers (fibres) in the oxygenator that separate the gas phase from the blood phase in the oxygenator, increasing the risk of air being aspirated into the blood across the barriers.

In some embodiments, the monitoring arrangement is configured to measure the line pressure upstream of any outlet pumps.

In some embodiments, the controller comprises a processor and software instructions implemented by the processor permitting it to control components of the control system.

In accordance with a second aspect of the present invention, there is provided a method of controlling the line pressure in a blood supply system as defined in claim 15.

In the blood supply system, a first pump is provided to pump blood from a reservoir via a primary passage at a flow rate and at a driving pressure toward a plurality of outlets, wherein one or more of the outlets are openable to permit flow through the outlet and closable to block flow through the outlet.

The method comprises the steps of determining a pressure value representative of a line pressure in the primary passage, and maintaining the line pressure in the primary passage above a pre-set level by controlling the first pump in response to the pressure value.

In some embodiments, the method comprises maintaining the line pressure in the primary passage above a minimum driving pressure, below a maximum driving pressure, and/or at a driving pressure.

In some embodiments, the method comprises the steps of determining a difference between the pressure value and the pre-set level, and issuing a signal to operate the first pump at pump parameters to reduce the difference, to adjust the line pressure in the primary passage to the pre-set level.

In some embodiments, the method comprises the steps of calculating an offset value representing a change of pump parameters effective to adjust the line pressure in the primary passage to the pre-set level, and generating the signal on the basis of the offset value.

In some embodiments, the method comprises the steps of providing one or more outlet pumps, using each outlet pump to transport blood through an outlet of the plurality of outlets, and modulating at least one outlet pump if the pressure value is below the pre-set level.

In some embodiments, the step of modulating at least one outlet pump is carried out prior to modulating the first pump.

In some embodiments, the method comprises preventing operation of at least one outlet pump if the pressure value is below the pre-set level.

In some embodiments, the method comprises modulating the first pump by altering revolutions per minute of the first pump.

In some embodiments, the method comprises using one or more pressure sensors to determine the pressure value.

In some embodiments, the method comprises measuring the line pressure downstream of the first pump.

In some embodiments, the method comprises measuring the line pressure upstream of an oxygenator.

In some embodiments, the method comprises measuring the line pressure upstream of any outlet pumps.

DESCRIPTION OF THE FIGURES

Exemplary embodiments of the invention will now be described with reference to the Figures, in which.

DESCRIPTION

Figure 1:
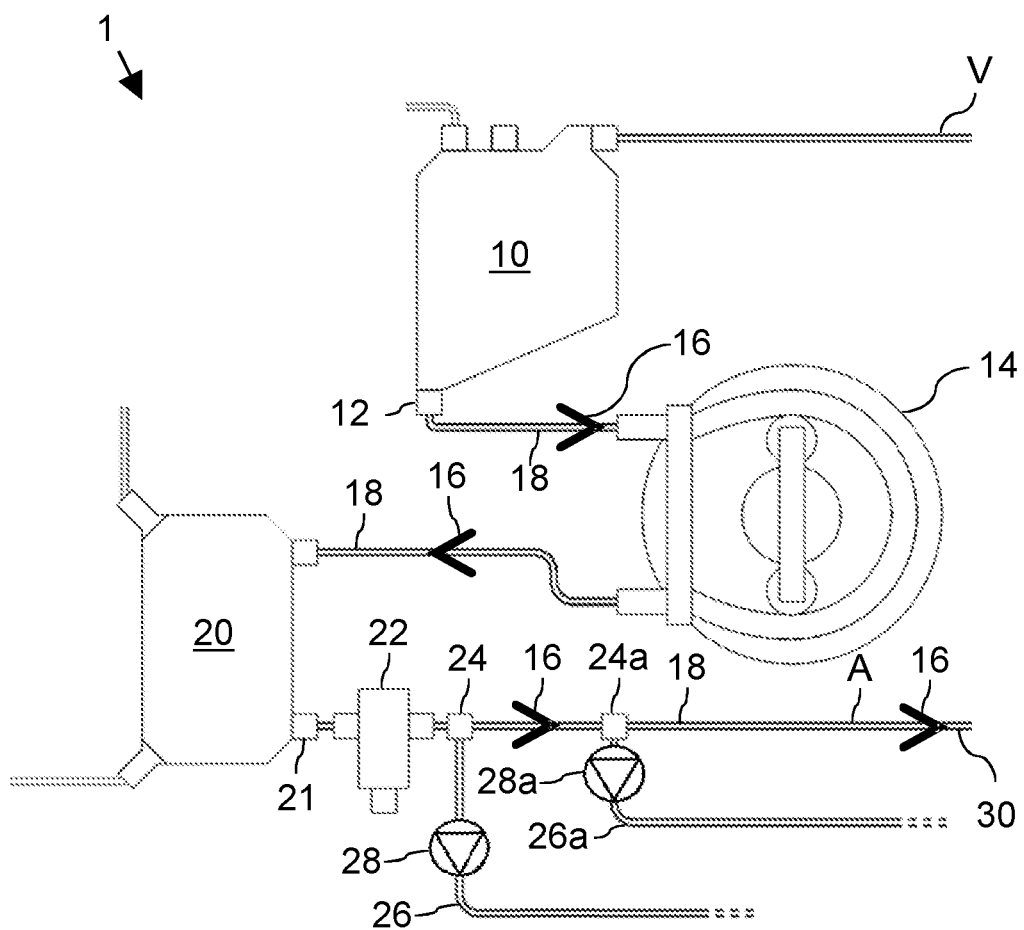
FIG. 1 shows a schematic arrangement of components of a control system for controlling the line pressure in a blood supply system in accordance with some embodiments of the present invention.

FIG. 1 shows components of a perfusion system 1 providing extracorporeal blood circulation and blood oxygenation. A venous line V is provided upstream of a blood reservoir 10 to receive venous (oxygen-reduced) blood from a patient.

The blood reservoir 10 comprises a reservoir outlet 12 from which blood may be drawn by activation of a pump 14 located downstream of the blood reservoir 10 in a direction indicated by arrows 16. The pump 14, which may be, e.g., a peristaltic pump or a centrifugal pump, constitutes a first pump in the main line downstream of the reservoir 10. The blood is pumped from the blood reservoir 10 along the tubing 18 via an oxygenator 20, leaves the oxygenator 20 via an oxygenator outlet 21 and flows through a first outlet 30. Downstream of the oxygenator 20, the blood is oxygenated. The tubing 18 may be referred to as the main line or the arterial line A, and constitutes a primary passage.

The first outlet 30 may be understood as a point at which the blood is conditioned for subsequent delivery to a patient. The flow rate of the blood through the first outlet can be assumed to be determined by the pump speed of the pump 14. I.e., if the pump 14 is operated at a higher pump speed, the flow rate through the first outlet 30 increases correspondingly. If the pump 14 is operated at a lower pump speed, the flow rate through the first outlet 30 decreases correspondingly. Stopping the pump 14 will stop the arterial blood flow.

Downstream of the oxygenator 20 and upstream of the first outlet 30, the tubing 18 comprises a first Y-junction 24 into a second tubing 26. The second tubing 26 constitutes a secondary passage and comprises a secondary pump 28 which permits a portion of the blood to be drawn from the main line, i.e., from upstream of the first outlet 30.

Downstream of the first Y-junction 24, a second Y-junction 24a is located in the tubing 18, leading into a third tubing 26a. The third tubing 26a constitutes another secondary passage and comprises, similar to the second tubing 26, another secondary pump 28a.

The second tubing 26 and the third tubing 26a constitute a plurality of secondary passages, each permitting a portion of blood to be drawn, via their respective Y-junctions 24 and 24a, from upstream of the first outlet 30.

The secondary passages permit blood to be drawn for, e.g., use as a carrier fluid for cardioplegic (heart-arresting) agent, or as source of oxygenated blood for cerebral (or other organ) perfusion. The blood may be drawn into a secondary passage intermittently, as and when needed. Regardless of the underlying purpose and frequency of any blood diversions, the initiation of a blood diversion from the arterial line affects the line pressure in the primary passage.

A pressure transducer 22 is provided in the primary passage downstream of the oxygenator outlet 21. The pressure transducer 22 constitutes, or is part of, a pressure monitoring arrangement and is configured to measure the line pressure in the primary passage. A pressure sensor may be positioned to measure the pressure upstream of the oxygenator 20. There may be more than one pressure sensor to measure the line pressure at critical points in the primary passage.

The pressure is provided as an input to a controller (not shown in FIG. 1), which is configured to determine whether the line pressure, as determined by the pressure transducer 22, is below a predetermined range. If the line pressure is below the predetermined pressure range, the controller may issue a signal to the pump 14 to increase the pump rate, in order to maintain the line pressure within a predetermined range. The controller may issue a signal to one of the secondary pumps 28, 28a to prevent their operation until the line pressure is within the predetermined range. If the line pressure is within the predetermined range, the controller may permit operation of the secondary pumps 28 or 28a. Diversion of blood via the second tubing 26 and/or the third tubing 26a may have an effect on the line pressure in the arterial line. While blood is diverted via secondary passages, the controller continues to operate the pump 14 to maintain the line pressure at a pre-set level (within the predetermined range).

A mechanism to ensure a minimum line pressure regardless of the number of active diversions increases the safety of the perfusion system 1.

By providing a mechanism that allows the secondary pumps to be activated only if the line pressure is above a minimum level or within a pre-determined range, a negative line pressure gradient can be avoided and, for practical purposes, eliminated.

During open heart surgery, the first outlet 30 may be clamped and no longer supply the systemic bloodstream of a patient directly. The first outlet 30 may be repurposed as a cerebral perfusion line and be connected to a line supplying blood to the brain. The pump 14 may be modulated to supply blood at through the first outlet 30 a flow rate of 0.5 litres per minute to the blood.

Intermittently, the first Y-junction 24 may be opened (e.g., the secondary pump 28 may be actuated) to allow blood to be diverted by a secondary pump 28 via the second tubing 26 for use in a cardioplegia line, to suppress heartbeat. The cardioplegia line may be constituted by the second tubing 26. The cardioplegia line may draw blood at a flow rate of around 0.2 to 0.3 l/m. The pressure transducer 22 monitors the pressure downstream of the oxygenator. If the pressure falls below the minimum line pressure, the controller sends a signal to the pump 14 to increase the pump speed to maintain a minimum line pressure.

Alternatively or concurrently, the controller may send a signal to the secondary pump 28 preventing it from operating until the line pressure in the first tubing 18 is sufficiently high. Once the line pressure, as determined by the pressure transducer 22, is sufficiently high, the controller permits the secondary pump 28 to draw blood from the first tubing 18.

Figure 2:
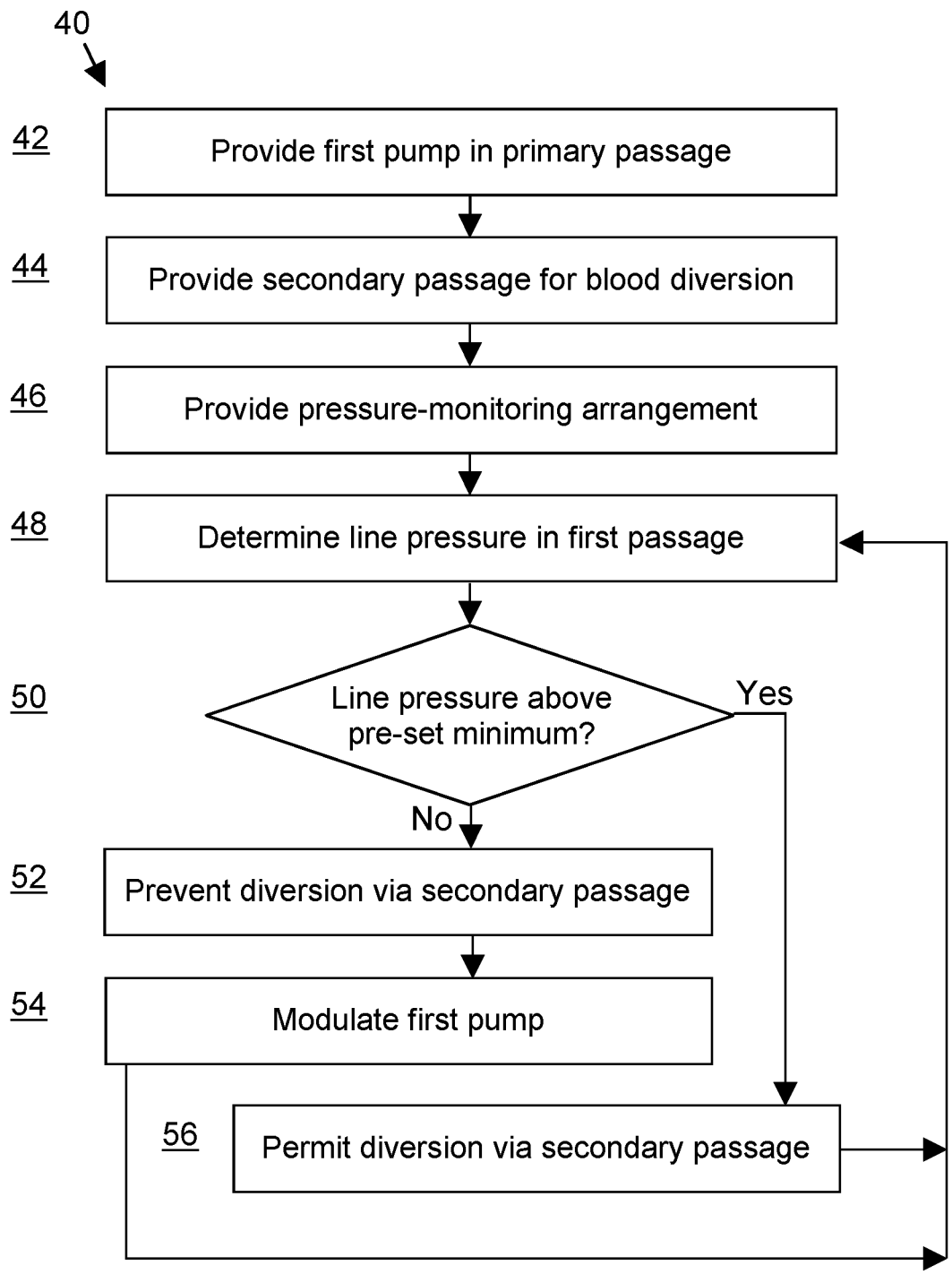
FIG. 2 shows steps of an exemplary sequence of steps of a method for controlling the line pressure in a blood supply system in accordance with some embodiments of the invention.

FIG. 2 shows steps of an exemplary method 40 for controlling the line pressure in a blood supply system. The controller (not shown) may be configured to carry out some or all steps of the method 40.

In step 42, a first pump is provided to transport blood in a primary passage from a blood reservoir towards and through a first outlet at a pre-determined flow rate and at a driving pressure. In step 44, a secondary passage is provided in the primary passage. The passages are closable (e.g., the primary passage may be clamped) and openable to allow blood to be diverted, according to clinical demand. It will be understood that any number of secondary passages may be provided. In step 46, a monitoring arrangement is provided to determine a pressure value representative of the line pressure in the primary passage. In step 48, the monitoring arrangement determines the line pressure in the primary passage. In step 50, a controller determines whether or not the pressure value is above a minimum line pressure.

If the pressure value is not above a minimum line pressure, then, in step 52, the controller prevents (or delays) flow via the secondary passage until operation of the first pump sufficiently increases the pressure value. In step 54, the controller may modulate the first pump to provide a line pressure above a minimum level or within a predetermined range. If the pressure value is at or above a minimum line pressure, then, in step 56, the controller allows blood to be diverted into the secondary passage. The controller loops back and evaluates the line pressure in the primary passage. Step 52 may be omitted if it can be ensured, by carrying out step 54, that the first pump is always modulated to maintain the line pressure above a pre-set level.

The effect on line pressure of a blood diversion into a secondary passage may be more pronounced when the flow rate in the primary passage is not much higher than the flow demand of the one or more secondary passages. The control system ensures that the first pump will turn enough to maintain sufficient line pressure in the main line during flow diversions. This allows a positive line pressure gradient to be ensured even at low flow rates through the first outlet, regardless of the number of active flow diversions.

The invention claimed is:

1. A control system controlling the line pressure in a blood supply system in which a first pump is provided to pump blood from a reservoir via a primary passage at a flow rate and at a driving pressure toward a plurality of outlets, wherein at least one outlet is openable to permit flow through the outlet and closable to block flow through the outlet, wherein the control system comprises:
   a monitoring arrangement to determine a pressure value representative of a line pressure in the primary passage, and
   a controller responsive to the monitoring arrangement, the controller configured to control the first pump to maintain the line pressure in the primary passage above a pre-set level, wherein the controller is configured to prevent opening of at least one outlet while there is not sufficient line pressure to avoid a negative line pressure when opening an outlet.

2. The control system according to claim 1, wherein the controller is configured to control the first pump to maintain the line pressure in the primary passage at a pressure level selected from the group consisting of: above a minimum driving pressure, below a maximum driving pressure, and at a driving pressure.

3. The control system according to claim 2, wherein the controller is further programmed to execute decision logic which is configured to reduce the difference by calculating an offset value representing a change of pump parameters effective to adjust the line pressure in the primary passage to the pre-set level, and by generating the signal on the basis of the offset value.

4. The control system according to claim 1, wherein the controller is configured to receive as an input the pressure value and is programmed to execute decision logic for determining a difference between the pressure value and the pre-set level, and for issuing a signal to operate the first pump at pump parameters to reduce the difference, to adjust the line pressure in the primary passage to the pre-set level.

5. The control system according to claim 1, further comprising at least one second outlet pump, the at least one second outlet pump provided to transport blood through an outlet of the plurality of outlets, wherein the controller is configured to modulate operation of the at least one second outlet pump if the pressure value is below the pre-set level.

6. The control system according to claim 5, wherein the controller is configured to modulate operation of the at least one second outlet pump prior to modulating operation of the first pump.

7. The control system according to claim 5, wherein the controller is configured to prevent operation of the at least one second outlet pump if the pressure value is below the pre-set level.

8. The control system according to claim 1, wherein the controller is configured to control the first pump by modulating revolutions per minute of the first pump.

9. The control system according to claim 1, wherein the monitoring arrangement comprises one or more pressure sensors.

10. The control system according to claim 1, wherein the monitoring arrangement is configured to measure the line pressure at at least one location selected from the group consisting of: downstream of the first pump, upstream of an oxygenator, downstream of an oxygenator, and upstream of any outlet pumps.

11. The control system according to claim 1, wherein the controller comprises a processor and software instructions implemented by the processor permitting it to control components of the control system.

12. The control system according to claim 1, comprising a configuration allowing, while the line pressure is above the pre-set level, an outlet to be opened even though the first pump is not active.

13. A method of controlling the line pressure in a blood supply system in which a first pump is provided to pump blood from a reservoir via a primary passage at a flow rate and at a driving pressure toward a plurality of outlets, wherein at least one outlet is openable to permit flow through the outlet and closable to block flow through the outlet, wherein the method comprises the steps of:

determining a pressure value representative of a line pressure in the primary passage, maintaining the line pressure in the primary passage above a pre-set level by controlling the first pump in response to the pressure value, and preventing opening of at least one outlet while there is not sufficient line pressure to avoid negative line pressure when opening an outlet.

14. The method according to claim 13, further comprising maintaining the line pressure in the primary passage at a pressure level selected from the group consisting of: above a minimum driving pressure, below a maximum driving pressure, and at a driving pressure.

15. The method according to claim 13, further comprising the steps of:

determining a difference between the pressure value and the pre-set level, and issuing a signal to operate the first pump at pump parameters to reduce the difference, to adjust the line pressure in the primary passage to the pre-set level.

16. The method according to claim 15, further comprising the steps of:

calculating an offset value representing a change of pump parameters effective to adjust the line pressure in the primary passage to the pre-set level, and generating the signal on the basis of the offset value.

17. The method according to claim 13, further comprising the steps of:

providing at least one second outlet pump, using the at least one second outlet pump to transport blood through an outlet of the plurality of outlets, and modulating the at least one second outlet pump if the pressure value is below the pre-set level.

18. The method according to claim 17, wherein the step of modulating at least one second outlet pump is carried out prior to modulating the first pump.

19. The method according to claim 17, further comprising preventing operation of at least one second outlet pump if the pressure value is below the pre-set level.

20. The method according to claim 13, further comprising modulating the first pump by altering revolutions per minute of the first pump.

21. The method according to claim 13, further comprising measuring the line pressure at at least one location selected from the group consisting of:

downstream of the first pump, upstream of an oxygenator, downstream of an oxygenator, and upstream of any outlet pumps.

22. The method according to claim 13, further comprising allowing, while the line pressure is above the pre-set level, an outlet to be opened even though the first pump is not active.

\* \* \* \* \*